United States Patent
Luo et al.

(10) Patent No.: US 10,233,482 B2
(45) Date of Patent: Mar. 19, 2019

(54) MICRO-FLUIDIC MIXER AND METHOD OF DETERMINING PATHOGEN INACTIVATION VIA ANTIMICROBIAL SOLUTIONS

(71) Applicants: The United States of America, as represented by the Secretary of Agriculture, Washington, DC (US); University of Maryland, College Park, MD (US)

(72) Inventors: Yaguang Luo, Bethesda, MD (US); Boce Zhang, Olney, MD (US); Patricia D. Millner, Burtonsville, MD (US)

(73) Assignees: The United States of America, as represented by The Secretary of Agriculture, Washington, DC (US); University of Maryland, College Park, MD (US)

( * ) Notice: Subject to any disclaimer, the term of this patent is extended or adjusted under 35 U.S.C. 154(b) by 648 days.

(21) Appl. No.: 14/849,034

(22) Filed: Sep. 9, 2015

(65) Prior Publication Data
US 2016/0068883 A1    Mar. 10, 2016

Related U.S. Application Data

(60) Provisional application No. 62/048,507, filed on Sep. 10, 2014.

(51) Int. Cl.
*B01L 3/00*    (2006.01)
*G01N 1/10*    (2006.01)
(Continued)

(52) U.S. Cl.
CPC .............. *C12Q 1/18* (2013.01); *B01F 5/0619* (2013.01); *B01F 5/0647* (2013.01);
(Continued)

(58) Field of Classification Search
CPC . B01L 3/00; G01N 1/10; G01N 33/18; C12Q 1/18
(Continued)

(56) References Cited

U.S. PATENT DOCUMENTS

2004/0252584 A1* 12/2004 Ji ........................ B01F 5/0646
366/341
2005/0047274 A1*  3/2005 Moser .................. B01F 5/0612
366/336

(Continued)

*Primary Examiner* — Brian J. Sines
(74) *Attorney, Agent, or Firm* — John D. Fado; Robert D. Jones

(57) ABSTRACT

A sample of produce wash water containing an antimicrobial sanitizer fluid, and a reference pathogen fluid are both injected into a pathogen inactivation region of a micro-fluidic mixer. The produce wash water (i.e. sanitizer fluid/pathogen fluid mix) is directed through mixer elements in the pathogen inactivation region of the micro-fluidic mixer. In the sanitizer deactivation region, a sanitizer deactivation solution is added to the sanitizer fluid/pathogen fluid mix to produce a deactivated solution. The deactivated solution is evaluated for the presence of the pathogen and the characteristics of the sanitizer. In the preferred embodiment, the sanitizer comprises chlorine and the pathogen comprises *E. coli* bacteria.

7 Claims, 9 Drawing Sheets
(2 of 9 Drawing Sheet(s) Filed in Color)

(51) Int. Cl.
  *C12Q 1/18*    (2006.01)
  *G01N 33/18*   (2006.01)
  *B01F 5/06*    (2006.01)
  *B01F 13/00*   (2006.01)

(52) U.S. Cl.
  CPC ......... *B01F 13/0059* (2013.01); *G01N 33/18* (2013.01); *B01F 2005/0636* (2013.01); *B01L 3/5027* (2013.01)

(58) Field of Classification Search
  USPC .......................... 422/502, 503; 436/180, 174
  See application file for complete search history.

(56) References Cited

U.S. PATENT DOCUMENTS

| | | | |
|---|---|---|---|
| 2006/0262642 A1* | 11/2006 | Park ..................... | B01F 5/0475 366/340 |
| 2007/0263477 A1* | 11/2007 | Sudarsan ............. | B01F 5/0644 366/3 |
| 2007/0263485 A1* | 11/2007 | Yang ..................... | B01F 5/061 366/336 |
| 2012/0300576 A1* | 11/2012 | Li ......................... | B01F 5/0646 366/338 |
| 2013/0260474 A1* | 10/2013 | Chan ..................... | G01N 1/38 436/174 |

* cited by examiner

MICRO-FLUIDIC MIXER AND METHOD OF DETERMINING PATHOGEN INACTIVATION VIA ANTIMICROBIAL SOLUTIONS

REFERENCE TO RELATED APPLICATIONS

This application claims the benefit of U.S. Provisional Application No. 62/048,507, filed Sep. 10, 2014, which is incorporated herein by reference in its entirety.

FIELD OF THE INVENTION

The disclosed method and apparatus relates to pathogen inactivation kinetics in a solution. Specifically, the method and apparatus described herein relates to a means of determining whether sufficient free chlorine is present in a wash solution to inactivate a target pathogen.

BACKGROUND OF THE INVENTION

Since the 1996 *Escherichia coli* (*E. coli*) O157:H7 outbreak, when nearly 10,000 people were sickened, foodborne illness has become a more visible threat to the public health. Almost two decades later, microbial contamination remains one of the most serious challenges for assuring the safety of food supplies. In 2011, the Centers for Disease Control and Prevention (CDC) estimated that roughly 48 million people are sickened by food-borne pathogens each year, including 3,000 cases ending in deaths.

Among all food categories, fruits and vegetables have emerged as the most significant vector of food borne bacterial pathogens because they are frequently consumed raw. Washing is an important step during fresh-cut produce processing as it removes the debris, soils, and produce latex released from the cut edges and maintains quality and shelf life of the final products, and can reduce 1-2 log cfu/g microbial loads.

Maintaining a high level of sanitizer in wash water is a practical challenge to the produce industry due to the rapid reaction of organic matter with sanitizers, especially the widely used hypochlorous acid (chlorine). As a result of its reaction with organic materials present in the wash water, free chlorine concentration usually declines rapidly during fresh produce wash operations.

Determination of the minimum free chlorine concentration needed to prevent pathogen survival/cross-contamination during produce washing is essential for the development of science-based food safety regulations and practices. Although the trend of chlorine concentration-contact time on pathogen inactivation is generally understood, specific information on chlorine and the kinetics of pathogen inactivation (particularly at less than 1 second) is urgently needed by the produce processing industry. However, conventional approaches to obtain this critical data have been unable to adequately measure very rapid responses.

The need exists for a quick and accurate means of determining the adequacy of chlorine wash solutions. The current disclosure is directed to a novel micro-fluidic device that is able to make the required determination in times as short as 0.1 second.

The micro-fluidic mixer described herein comprises one inlet each for bacterial, chlorine and dechlorinating solutions, and one outlet for effluent collection. To determine the kinetics of free chlorine on pathogen inactivation, chlorine solutions of varying concentrations are pumped into the micro-fluidic mixer. A sample bacterial solution is injected into the mixer through a separate inlet.

After mixing, a dechlorinating solution is injected into the mixer to stop the chlorine-pathogen reaction. The effluent is collected and the surviving bacteria cells are enumerated using a modified 'Most Probable Number' method. Free chlorine concentration is determined using a standard colorimetric method. The contact time is precisely controlled by adjusting the solution flow rate and quantitatively determined by computational fluid dynamics modeling.

SUMMARY OF THE INVENTION

This disclosure is directed to a micro-fluidic sanitizer analysis system. The system comprises a micro-fluidic mixer with a pathogen inactivation region, and a sanitizer inactivation region. The system is structured so that a sanitizer fluid mixes with and at least partially inactivates a reference pathogen fluid in the pathogen inactivation region. The sanitizer fluid/pathogen fluid mix is then directed to the sanitizer inactivation region, where the sanitizer is inactivated to produce an inactivated sanitizer fluid. The inactivated sanitizer fluid is analyzed for a presence of the pathogen and characteristics of the inactivated sanitizer fluid.

The disclosure is further directed to a method of mixing a sanitizer solution with a reference pathogen fluid. In accordance with the method, a sanitizer fluid is injected into a sanitizer fluid inlet, and a pathogen fluid is directed into a pathogen fluid inlet. The sanitizer fluid and the pathogen fluid converge at a first y-injection mixer so that the first y-injection mixer mixes the sanitizer fluid and the pathogen fluid. The sanitizer fluid/pathogen fluid mix then flows into a first Dean's vortex mixer. The sanitizer fluid/pathogen fluid mix is then directed into a second y-injection mixer where it is blended with a sanitizer deactivation fluid to create a deactived fluid. The deactivated fluid then flows into a second Dean's vortex mixer. After the second Dean's vortex mixer the deactivated fluid flows out of the micro-fluidic mixer where it is analyzed for the presence of the pathogen and the characteristics of the sanitizer fluid.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

DETAILED DESCRIPTION OF PREFERRED EMBODIMENTS

Figure 1:
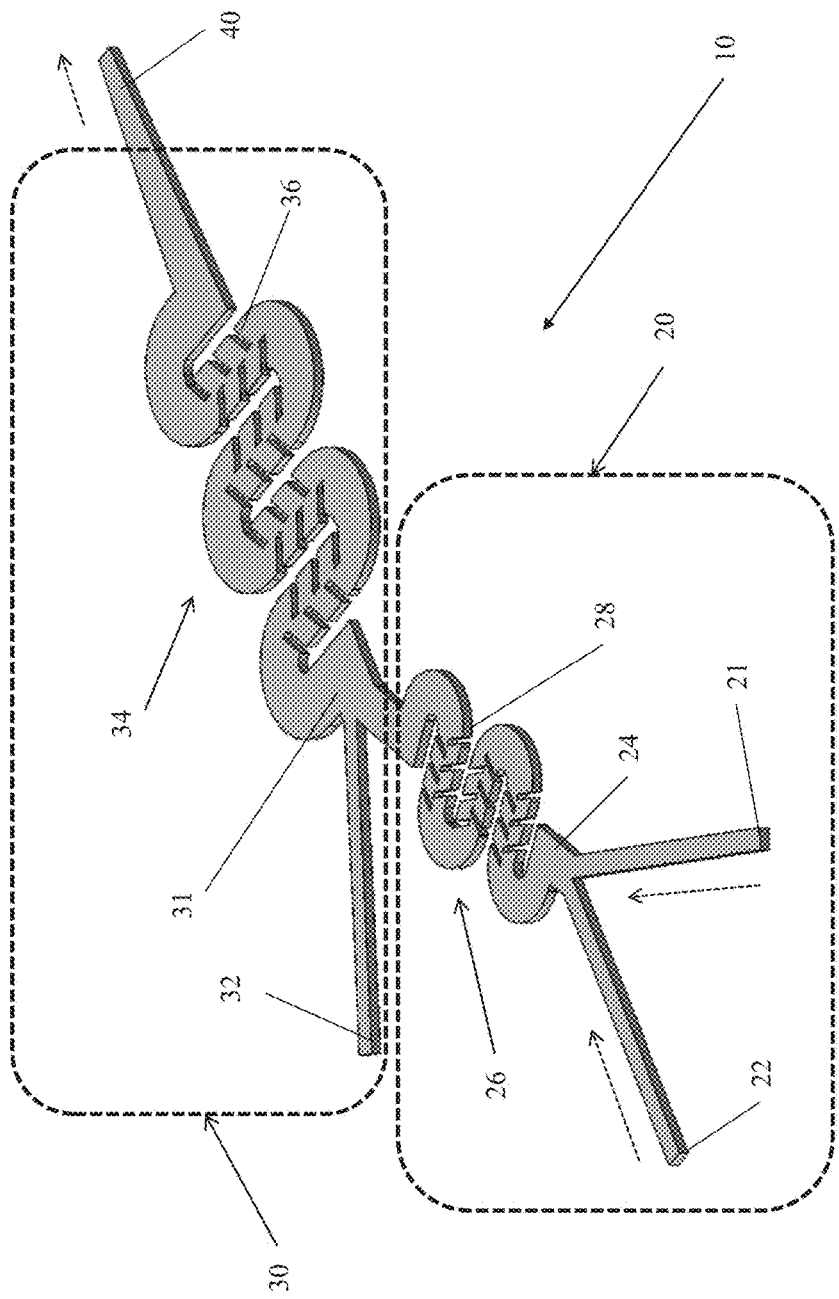
FIG. 1 is an elevational schematic of the micro-fluidic mixer described herein.
Figure 2:
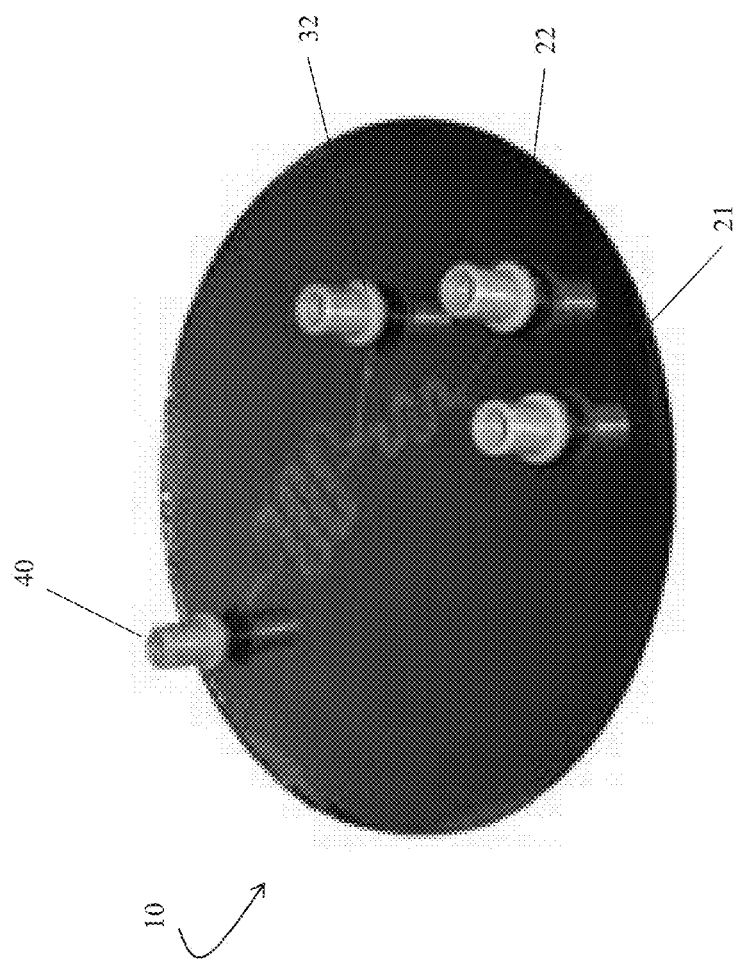
FIG. 2 is a (black and white) photograph of the micro-fluidic mixer described herein.

As generally shown in FIG. 1, the current invention is directed to a micro-fluidic mixer 10. The micro-fluidic mixer 10 comprises two mixing regions 20, 30. The first region generally comprises a bacterial pathogen inactivation region 20, and the second region comprises a dechlorination region 30.

As shown in FIG. 1, the pathogen inactivation region 20 is designed to mix a sample of produce wash water with a reference bacterial source. The combined wash water and bacterial solution leaving the pathogen inactivation region 20 is directed into the dechlorination region 30. In dechlorination region 20, a chlorine inactivating solution (i.e. a dechlorinating solution) is added to the fluid mix to inactivate the chlorine in the solution. From the dechlorination region 30, the effluent flows out an outlet 40. The effluent leaving the outlet 40 is examined to determine the quantity of surviving bacteria cells in the effluent.

Specifically, as shown in FIG. 1, the pathogen inactivation region 20 comprises a first inlet 21 and a second inlet 22. A bacterial reference sample solution is injected into the first inlet 21. In the preferred embodiment, the bacterial sample solution comprises *Escherichia coli* (i.e. *E. coli*) O157:H7 (RM4406, ATCC 700728), but other types of bacteria or contaminant should be considered within the scope of the invention. A sample of produce wash water (or other studied solutions) is injected in the second inlet 22. The dashed-line arrows shown in FIG. 1 indicate the direction of fluid flow.

The bacterial fluid and the wash water converge at a Y injection-mixer 24. The fluid is then directed though a Dean's vortex-mixer 26 configuration to thoroughly mix the wash water and bacterial fluids. The Dean's vortex mixer 26 includes chaotic mixer elements 28 that extend into the mixer's 28 main channels and create turbulence that further mixes the fluids.

As the fluid leaves pathogen inactivation region 20 and enters the dechlorination region 30, the fluid flows into a second y-injection mixer 31. In the (second) y-injection mixer 31 the fluid is mixed with a dechlorination fluid entering from a dechlorination fluid inlet 32. The dechlorination fluid is mixed with the bacteria/wash water mix in a (second) Deans vortex 34 which also includes a (second) set of chaotic mixer elements 36. The (now) dechlorinated fluid flows out the outlet 40 where any surviving bacteria are analyzed.

FIG. 2 shows a picture of the micro-fluidic mixer 10, as fabricated. The device was fabricated and assembled using modified microfabrication methods that are well known in the art. The master mold was fabricated on a silicon wafer with SU-8 microchannels via contact photolithography using a mask aligner according to the supplier's instruction. Polydimethylsiloxane (PDMS) replicas with patterned microchannels were prototyped via soft lithography by curing the PDMS mixture (base: curing agents=10:1) on the mast mold at 125° C. for 20 minutes. Cured replicas were further assembled into the micro-fluidic mixer on a clean silicon wafer via $O_2$ plasma treatment (March Jupiter III, Westlake, Ohio, USA).

FIG. 2 shows the bacteria solution port 21, wash water solution port 22, and the dechlorination solution 32 port, as well as the effluent outlet port 40. The inlet ports 21, 22, 32, and the outlet port 40 were created using Nanoports (IDEX Health and Science, Oak Harbor, Wash., USA) to provide seamless connection with an external syringe pump, which allows adjustable flow rate.

Upon successful assembly of the device 10, the micro-fluidic mixer 10 was initially evaluated for its effectiveness and accuracy in providing a constant, stable input of solutions through the microchannel. The stability of bacterial concentration was tested by pumping the bacterial suspension (via bacteria inlet 21, FIGS. 1 and 2) and sterile water (via inlet wash water inlet 22 and dechlorination fluid inlet 32, FIGS. 1 and 2) at different flow rates. The effluent was collected and the bacteria were enumerated using modified 'Most Probable Number' (MPN) procedures as described in the following section. The chlorine stability was tested similarly by pumping chlorine solution (via wash water inlet 22) with water, and the effluent was collected to quantify chlorine concentration using the DPD colorimetric method. In the follow-up chlorine stability test and dechlorinating efficiency studies, both chlorine (via wash water inlet 22) and dechlorinating solutions (via dechlorination inlet 32) were pumped into the micro-fluidic mixer with water. The effluent was collected to detect chlorine residual using the DPD method.

The mixing efficiency and mixing patterns were evaluated by modeling scalar mixing (mixing efficiency) using the Computational Fluid Dynamics software (Autodesk Simulation CFD, 2014). The chlorine diffusion coefficient in water used in this modeling was $1.38\times10^{-5}$ $cm^2/s$. The solution has a low Reynolds number in this device, and the liquid was determined to be incompressible and the flow was characterized as laminar in the scalar mixing model. The boundary conditions (i.e. inlet volume flow rate, and outlet pressure) were adjusted to reflect the actual experimental value.

The contact time between bacteria and chlorine solution was defined as the time required to pass through the pathogen deactivation region 20 (FIG. 1). The contact time was precisely controlled by adjusting the flow rate of the syringe pump that supplied the fluid to the micro-fluidic mixer 10. The mixing efficiency (scalar mixing) of the device and contact time distribution also were determined quantitatively using the trace function in the CFD software.

Pathogen Inactivation Study

A series of chlorine solutions with free chlorine concentrations of 0.5, 1, 5, 10, 20, 50 mg/L were freshly prepared using sodium hypochlorite. The free chlorine concentration before and after tests were verified using chlorine photometer (CP-15, HF Scientific Inc., Ft. Myers, Fla., USA). To determine the kinetics of chlorine on pathogen inactivation, chlorine solutions were pumped into the micro-fluidic mixer, together with the bacterial suspension of *E. coli* O157:H7 through a separate inlet. This was followed by injection of dechlorinating solution at the entry to Region B to stop the chlorine-pathogen reaction. To consider a dilution effect inside the micro-fluidic mixer (pathogen deactivation region 20, FIG. 1), the chlorine concentration in the start solution was double the effective concentration in the microchannel. All concentrations discussed in the study are effective concentrations after considering the dilution factors.

The dechlorinating solution containing 0.1% sodium pyruvate and dechlorinating reagent (containing 1~10% sodium thiosulfate and 90~99% sodium sulfate) was pumped via the dechlorination inlet 32 (FIG. 1) to stop the inactivation process. The contact time was controlled precisely by adjusting the solution flow rate and was determined quantitatively by CFD modeling. Pathogen survival was quantified using a modified 'Most Probable Number' method as detailed in the inventors' previous publications.

All experiments were repeated at least three times, and data was analyzed using SAS software (Version 9.3). *E. coli* O157:H7 populations were subjected to log transformation before statistical analysis. Data was analyzed as a two-way analysis of variance (ANOVA) with treatment and contact time as the main factors. Assumptions of normality and variance homogeneity were checked and the variance grouping technique was used to correct for variance heterogeneity. When effects were statistically significant, means comparisons were done using Tukey's range test with adjusted p-values to maintain experiment-wise error of ≤0.05.

Results

Figure 3:
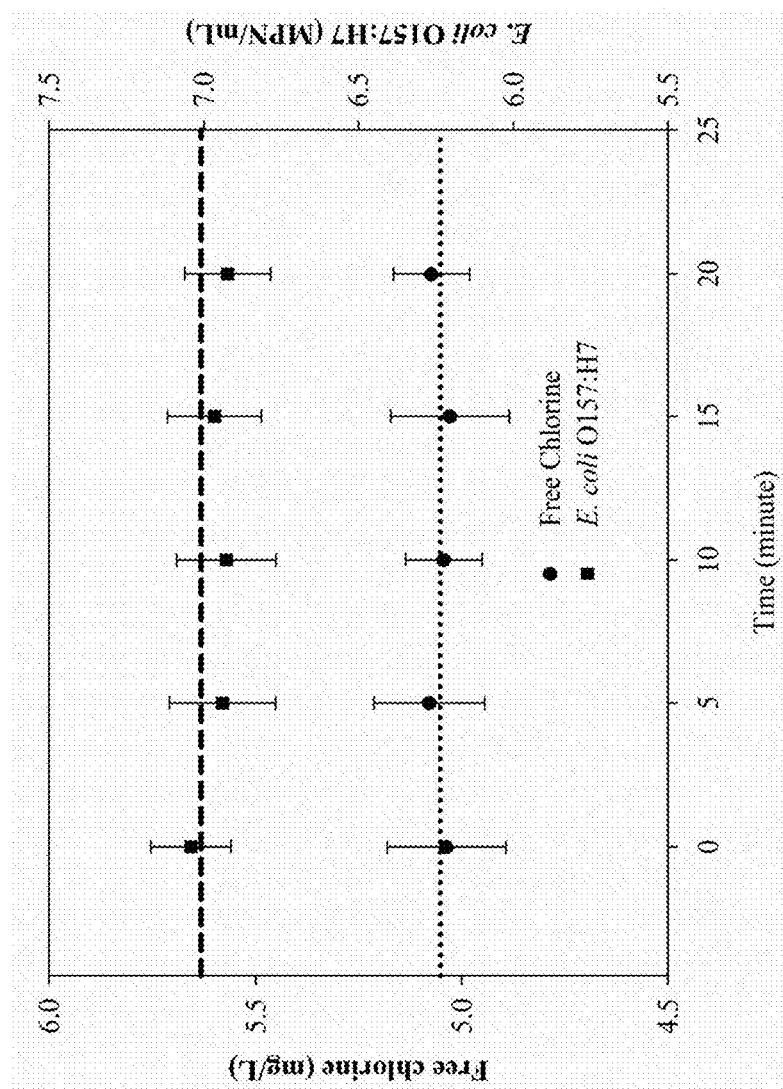
FIG. 3 shows the chlorine concentration and bacterial suspension during a test period.
Figure 4:
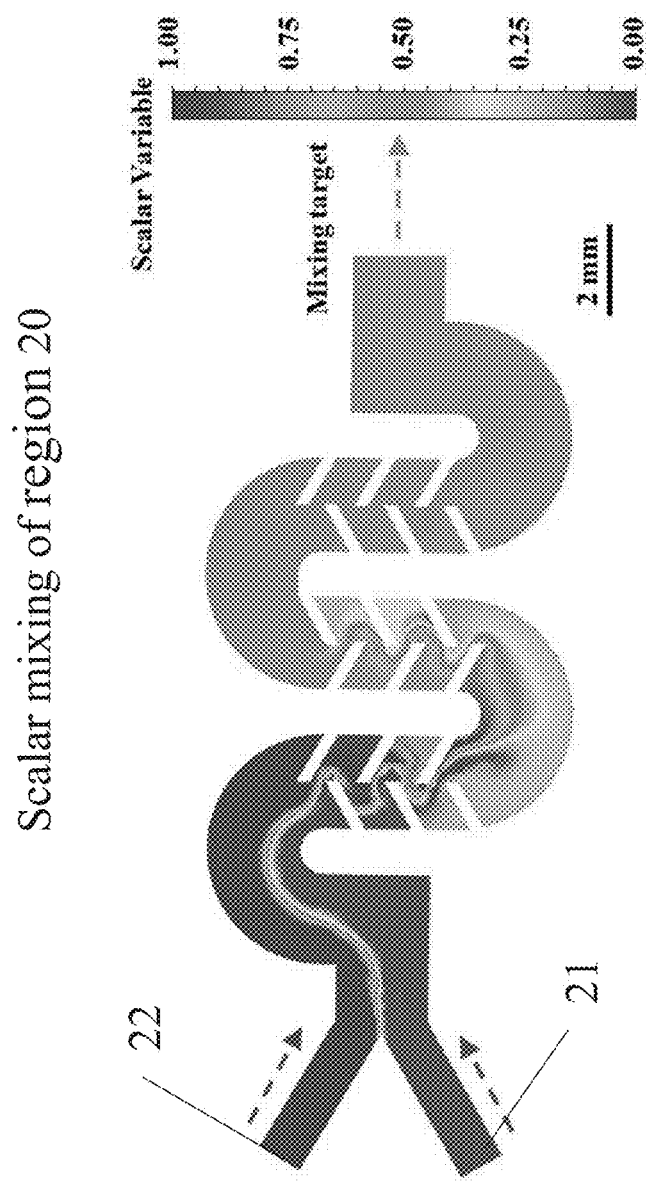
FIG. 4 is a schematic view of the computational fluid dynamics modeled mixing of bacteria, chlorine, and neutralizing solutions inside the micro-fluidic mixer (described herein) at a flow rate equivalent to 0.75 contact time.
Figure 5:
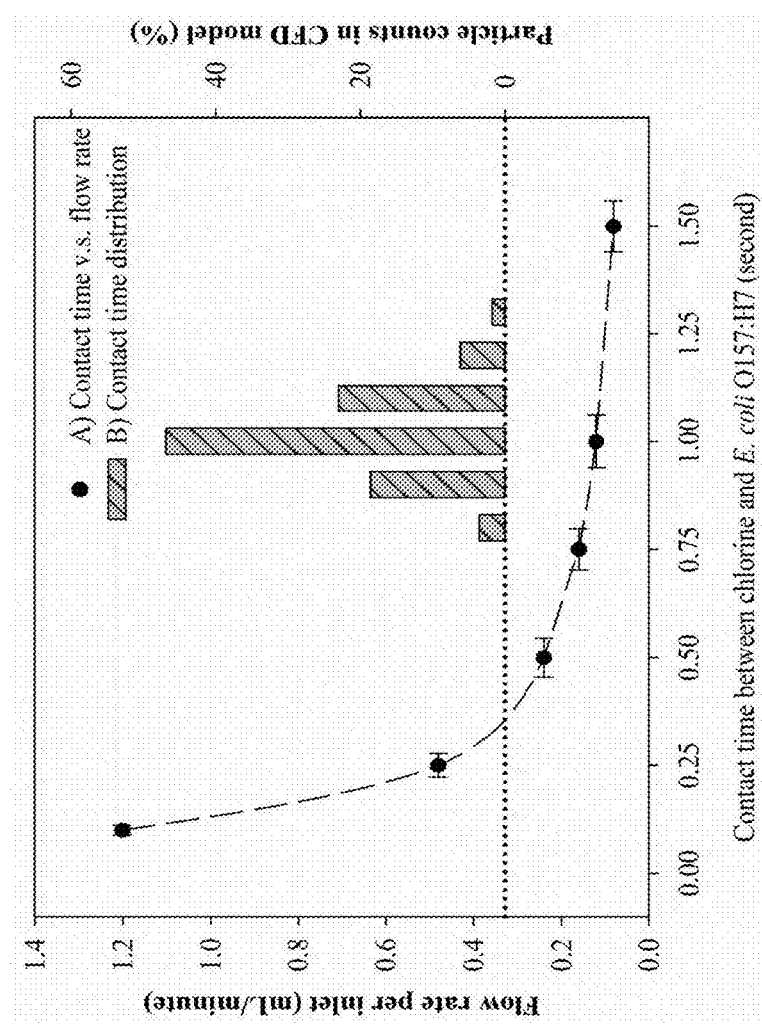
FIG. 5 is a graph showing the correlation between volumetric flow rate and contact time.

The effectiveness of the micro-fluidic mixer in maintaining stable concentrations of chlorine and bacterial suspensions during pumping was validated. The stability of the solution delivery first was tested by separately pumping chlorine (via wash water inlet 22, FIG. 1) with water, and then bacterial suspension (bacteria inlet 21, FIG. 1) with water, and collecting the effluent of each independent test for quantification. As shown in FIG. 3, both chlorine concentration (5 mg/L) and bacterial suspension ($10^7$ MPN/mL) were stable for the entire 20 minute test period during continuous pumping at a flow rate of 0.16 mL/minute, or the equivalent of a 0.75 second contact time. The deviation of chlorine concentration was no more than 3%. *E. coli* O157:H7 concentrations were less than 2.5% (FIG. 3) from the respective theoretical values.

The mixing efficiency of the pathogen inactivation region 20 and the dechlorination region 30 (FIG. 1) was also validated in separated experiments. The total pathogen inactivation (negative control) was validated by mixing chlorine (50 mg/L) and pathogen solution ($10^8$ MPN/mL) inside the micro-fluidic mixer without the addition of dechlorinating solution, resulting in no bacterial survival detected from the collected effluent. The neutralizing power of dechlorinating reagent was demonstrated when pumping both chlorine and dechlorinating solutions into the micro-fluidic mixer, which resulted in no chlorine residue being detected in the collected effluent. These results are consistent with other reported micro-fluidic mixer studies with different solutions and flow rates.

The mixing efficiency and mixing pattern were studied using CFD modeling of scalar mixing. During the modeling process, all solutions were considered as Newtonian fluids with non-slip boundary conditions. The solution has a low Reynolds number and laminar flow characteristics, due to the small scale. Achieving efficient and rapid mixing is one of the challenging tasks in micro-fluidic mixers, because mixing under laminar flow conditions depends on slow diffusion of chemicals and bacterial cells.

Therefore, the study incorporated multiple passive micro-fluidic mixer designs that can be completed by simple modification of channel geometries into the following configurations: "Y" injection, serpentine channels, and channels with patterned grooves. These modifications and designs enhance folding, stretching and breaking of the laminar flows, which improves the mixing efficiency during flow. FIG. 4 shows the modeled scalar mixing of chlorine, bacteria, and dechlorinating solutions in our micro-fluidic mixer.

The modeled result indicated that mixing can be achieved very rapidly and efficiently in the inventors' design. Therefore, the micro-fluidic mixer provides the means to conduct studies on pathogen inactivation kinetics in time periods as brief as 0.1 second. The CFD modeling also indicated that increased flow rates which result in decreased contact time, could increase mixing efficiency.

The micro-fluidic mixer was also optimized for the adjustability of flow rate and contact time. By changing flow rate at different inlets, the time needed for fluid elements to pass through the mixing region can be varied. The relationship between the initial flow rate required and the specific contact time distribution can also be determined and predicted by the trace function in the CFD modeling software. FIG. 5 shows the correlation between inlet flow rate and contact time distribution. The micro-fluidic mixer had a channel dimension of 1 mm (width) by 0.1 mm (height), resulting in a cross-sectional area (A) of 0.1 $mm^2$. The travel distance (D) of the chaotic mixer was 10 mm. The contact time (t) can be adjusted by changing the flow rate (r), and is calculated as:

$$t=D\times A/r \tag{1}$$

Ideally, every fluid element entering mixing the pathogen deactivation region 20 (FIG. 1) should spend the same amount of time before it enters the dechlorination region 30 (FIG. 1). However, with the folding, stretching, and breaking of the laminar flow condition, different fluid elements took different amounts of time to pass through the mixing patterns. In reality, not all fluid elements spend the same amount of time passing through the mixing regions in the micro-fluidic mixer. However, the variation did not affect the precision of contact time control with the coefficient of variation ($C_V$)<0.05. The calculated flow rate was adopted in the following pathogen inactivation study to control the contact time from 0.1 to 1.5 seconds.

The effect of chlorine concentration and exposure time on *E. coli* O157:H7 inactivation was tested using the micro-fluidic mixer after validation tests were completed. As shown in FIG. 6, the inactivation of *E. coli* O157:H7 was significantly affected by free chlorine concentration (P<0.0001), exposure time (P<0.0001), and their interactions (P<0.0001). The chlorine concentration and contact time exhibited a negative relationship, i.e., more concentrated chlorine solution required less contact time to achieve a 5-log reduction. With an *E. coli* O157:H7 suspension solution containing $1\times10^8$ CFU/mL, 1.0 mg/L free chlorine solutions achieved 0.14 log reduction in 0.25 second, and 4.97 log reduction in 1.00 second. Increasing chlorine concentration significantly reduced exposure time required to achieve the same log reduction. With a free chlorine concentration of 10.0 mg/L, a 3.87 log reduction was achieved in 0.1 second, and a 5.77 log reduction in 0.25 second.

The determination of minimum effective free chlorine concentration required to prevent pathogen survival and cross-contamination during produce wash is a major challenge facing the produce industry and regulatory agencies. The US industry-wide hazard analysis and critical control points (HACCP) program has set 1 mg/L free chlorine as the critical control limit (CCP) previously. Recent studies have shown that this chlorine concentration is insufficient in preventing pathogen cross-contamination.

However, the effective minimum free chlorine concentration to prevent cross-contamination has not yet been determined and validated. During water-mediated cross-contamination, pathogens are first dislodged from the surface of the contaminated produce, survive in wash water, and then transfer to the originally uncontaminated produce as they move along with wash water. Therefore, the effective minimum free chlorine concentration required to prevent pathogen cross-contamination must be a concentration that can inactivate pathogens instantaneously. The inventors determined that a free chlorine concentration of 1 mg/L will achieve a 5-log reduction in 1.00 second, 5 mg/L in 0.50 second, and 10 and 20 mg/L in 0.25 second. Chlorine concentration at 0.5 mg/L and 50 mg/L were included in the study, but the accurate determination of exposure time required to achieve a 5-log reduction requires additional modification of the micro-fluidic mixer to accommodate such low and high chlorine concentrations.

Figure 7:
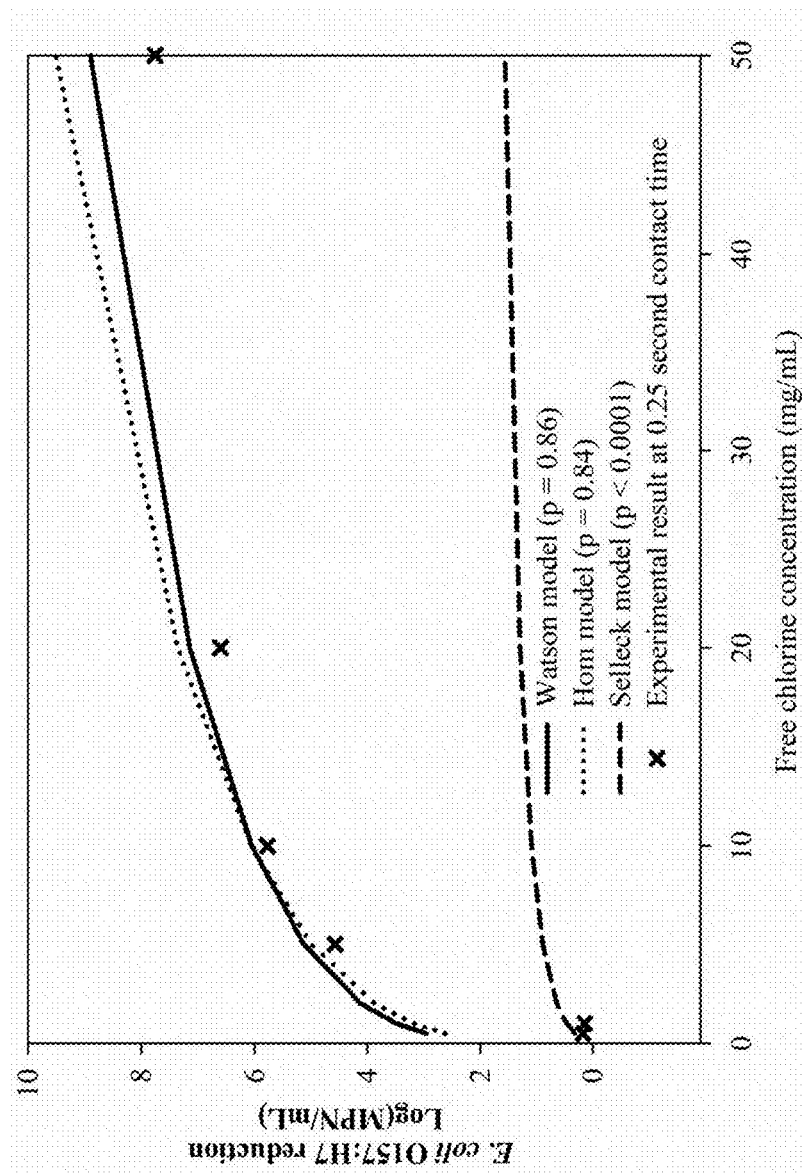
FIG. 7 is a graphic comparison of experimental test results to three selected bacterial inactivation models.

The results obtained with 1, 5, 10, and 20 mg/L in this study provide a reasonably good explanation for the observation that cross-contamination occurs at 1 mg/L, but not at 10 mg/L, as 1 mg/L requires more than 1.2 seconds to achieve a 5-log reduction in pathogen while 10 mg/L kills pathogens much faster (0.2 second for a 5-log reduction). The results were analyzed with the contour graph (FIG. 7), with the predicted log reduction (1-5 log) at different chlorine concentrations and contact times.

Kinetic Models

Kinetic modeling was also applied to simplify the complicated disinfection phenomena of produce wash system. Three models that are commonly used for studying bacterial disinfection kinetics with chemical-based disinfectant, including the Chick-Watson Model, the Hom Model, and the Selleck Model.

Watson developed an empirical logarithmic equation to relate the inactivation constant (k) to disinfectant concentration (C) and reaction time (t):

$$\log\left(\frac{N}{N_0}\right) = -kC^n t \quad (2)$$

where N=number of pathogen cells per unit volume,
$N_0$=number of pathogen cells initially at time zero,
k=strain- and condition-specific inactivation constant,
C=free chlorine concentration,
n=coefficient of dilution,
t=reaction (contact) time.

Figure 6:
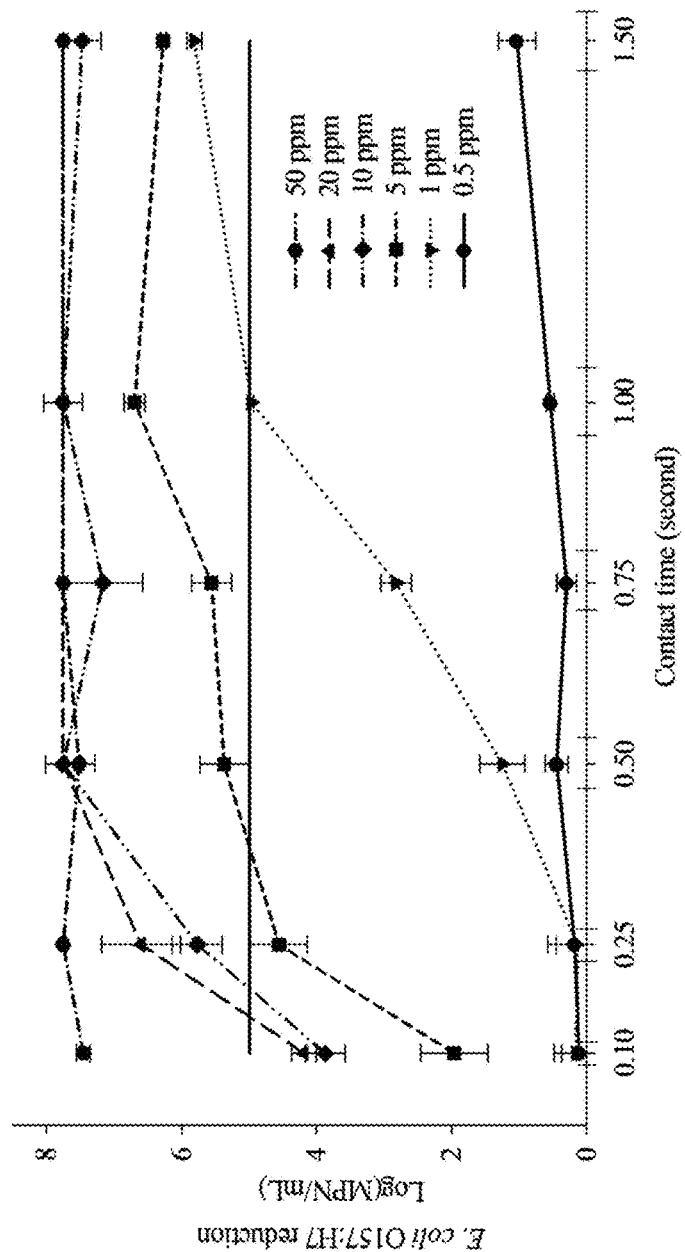
FIG. 6 is a graph showing the effects of chlorine concentration and contact time on log reductions of *E. coli*.

From the experimental data in FIG. 6, k and n were determined as:

$$\log\left(\frac{N}{N_0}\right) = -3.48 C^{0.24} t \quad (3)$$

The Hom model is a generalized empirical equation of the Chick-Watson model considering chlorine disinfection as a pseudo first-order reaction:

$$\log\left(\frac{N}{N_0}\right) = -kC^n t^m \quad (4)$$

where m is a reaction rate constant and other factors are as described above for equation 2. The constants were modeled using experimental data as:

$$\log\left(\frac{N}{N_0}\right) = -3.18 C^{0.28} t^{0.18} \quad (5)$$

The Selleck model was originally developed to predict chlorine inactivation of bacteria in wastewater. The model was empirical and can be adjusted to different sanitization systems:

$$\log\left(\frac{N}{N_0}\right) = -n\log\left(1 + \frac{Ct}{k}\right) \quad (6)$$

The experimental data also was applied to compute values of empirical coefficient k and n, which yields:

$$\log\left(\frac{N}{N_0}\right) = -0.678\log\left(1 + \frac{Ct}{0.25}\right) \quad (7)$$

Figure 8:
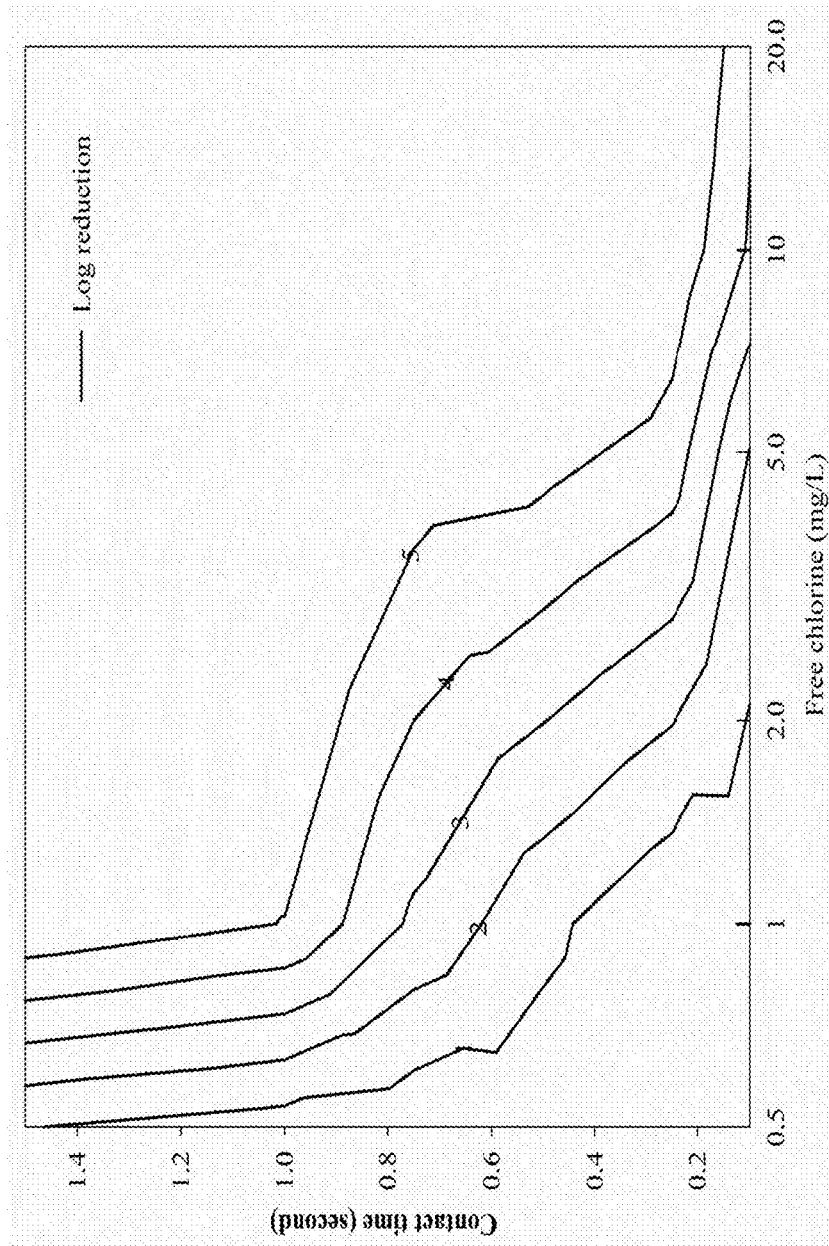
FIG. 8 is a contour graph of log reductions (1 to 5 log) of *E. coli* at different chlorine concentrations and contact times.

The pathogen inactivation kinetics of the three selected models were compared statistically with the original experimental data. FIG. 8 shows the effect of chlorine concentration at a specific contact time (0.25 second). Both the Watson (P=0.860) and Hom (P=0.841) models reflected the pathogen inactivation scenarios with short contact time. The Selleck model was used to predict pathogen survival in chlorine over a substantially longer contact time (e.g. 3 hours) than was used in the studies reported here. Thus it is not surprising that the model didn't fit the results from this short time-course kinetic study (P<0.0001). The variation and difference between experimental data and modeled results could be explained by the heterogeneity of bacterial cells in a population relative to their inherent resistance to chlorine, which was distributed in a spatially- or time-dependent manner.

Figure 9:
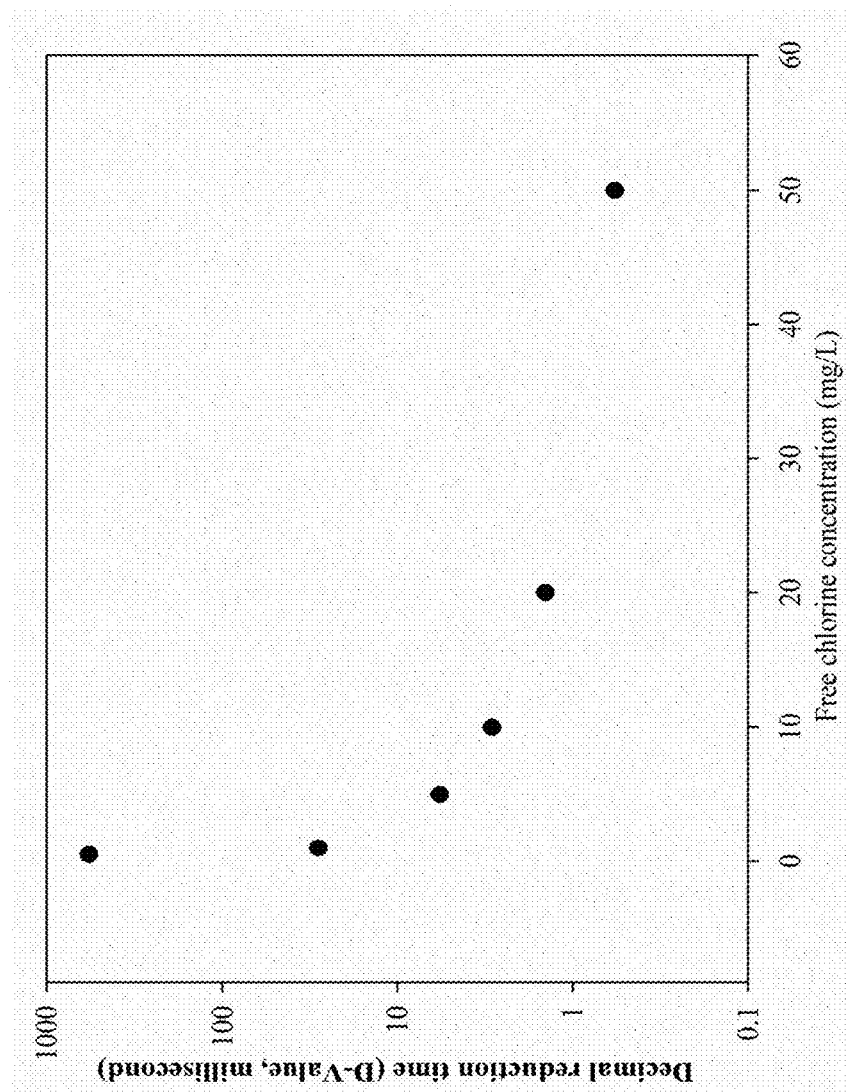
FIG. 9 is a decimal reduction time (D-value) required at certain free chlorine concentrations to achieve 90% (1-log reduction) of *E. coli* in water.

In a chlorine-based disinfection process, the decimal reduction time (D-value) is defined as the time required at a specified free chlorine concentration to kill 90% (one log reduction) of the organisms being studied. The D-value here was calculated based on the empirical models developed in this study, namely the Watson model (equation 3) and the Hom model (equation 5). FIG. 9 shows the relationship between chlorine concentration and D-value. For the widely used 1 mg/L free chlorine concentration in HACCP programs, the D-value is 28.06 milliseconds. By increasing chlorine concentration to 5, 10, and 20 mg/mL, the D-value reduces to 5.72, 2.87, and 1.43 milliseconds respectively.

Conclusions

A micro-fluidic mixer useful for assessing pathogen inactivation kinetics at less than 1 second was designed, fabricated, and validated. This device also was used to determine the time and dose dependent response of pathogen inactivation via free chlorine. Test results indicate that 1) *E. coli* O157:H7 inactivation is significantly affected by free chlorine concentration (P<0.0001), contact time (P<0.0001), and their interactions (P<0.0001); 2) A 5-log reduction of *E. coli* O157:H7 requires exposing *E. coli* O157:H7 cells to a solution containing 1 mg/L free chlorine for at least 1.2 seconds, or a solution containing 10 mg/L free chlorine for 0.2 second. These findings provide critical information regarding the determination of minimum free chlorine concentration required to prevent pathogen survival and cross-contamination during fresh produce wash operations.

For the foregoing reasons, it is clear that the method and apparatus described herein provides an innovative micro-fluidic mixer for determining whether sufficient free chlorine is present in a wash solution to inactivate a target pathogen. The disclosed method and apparatus may be modified and customized as required by a specific operation or application, and the individual components may be modified and defined, as required, to achieve the desired result.

Although all of the materials of construction are not described, they may include a variety of compositions consistent with the function described herein. Such variations are not to be regarded as a departure from the spirit and scope of this disclosure, and all such modifications as would be obvious to one skilled in the art are intended to be included within the scope of the following claims.

What is claimed is:

1. A micro-fluidic sanitizer analysis system comprising:
a pathogen inactivation channel comprising:
  (a) a first Y-injection mixer comprising a first and second inlets; and,
  (b) at least first and second S-shaped serpentine pathogen inactivation channels having chaotic mixer elements and being connected in series, a first end of the first S-shaped serpentine channel being connected to the first Y-injection mixer; and,
a sanitizer deactivation channel operatively connected to the pathogen inactivation channel, the sanitizer deactivation channel comprising:
  (c) a second Y-injection mixer comprising third and fourth inlets, a second end of the pathogen inactivation serpentine channels comprising the third inlet: and,
  (d) at least third and fourth sanitizer deactivation S-shaped serpentine channels having chaotic mixer elements and being connected in series, a first end of the sanitizer deactivation S-shaped serpentine channels being connected to the second Y-injection mixer, and a second end of the sanitizer deactivation S-shaped serpentine channels comprising a sanitizer deactivation channel outlet;
wherein the micro-fluidic system is configured so that after a produce wash sample is injected into the first or second inlet, the produce wash sample is mixed with a reference bacterial solution component in the first Y-injection mixer, and then directed to the third inlet, and then mixed with a sanitizer deactivating solution component in the second Y-injection mixer, and then the resulting deactivated sanitizer solution is directed out of the sanitizer deactivation channel outlet, the resulting deactivated sanitizer solution then being analyzed.

2. The micro-fluidic system of claim 1 wherein the system is structured so that: the first injection mixer, the first and second S-shaped serpentine pathogen inactivation channels, second Y-injection mixer, and third and fourth sanitizer deactivation S-shaped serpentine channels are all in fluid communication and are connected in series.

3. The micro-fluidic system of claim 1 wherein the system is structured so that the pathogen inactivation channel comprises at least one Dean's mixer.

4. The micro-fluidic system of claim 1 wherein the produce wash sample comprises a chlorine produce wash solution.

5. The micro-fluidic system of claim 1 wherein the reference bacterial solution component comprises *E. coli*.

6. The micro-fluidic system of claim 1 wherein the system comprises a continuous fluid channel, the pathogen inactivation channel having the same structure as the structure of the sanitizer deactivation channel.

7. The micro-fluidic system of claim 1 wherein the system is structured so that the pathogen inactivation channel comprises at least one Dean's mixer.

* * * * *